US012630889B2

(12) United States Patent
Esposito et al.

(10) Patent No.: US 12,630,889 B2
(45) Date of Patent: May 19, 2026

(54) APPARATUS AND METHOD FOR SAMPLING AND DETECTING A PATHOGEN IN AIR

(71) Applicants: ISTITUTO NAZIONALE DI ASTROFISICA, Rome (IT); UNIVERSITA' DEGLI STUDI DI ROMA "LA SAPIENZA", Rome (IT); ALMA MATER STUDIORUM—UNIVERSITA' DI BOLOGNA, Bologna (IT); UNIVERSITA' DEGLI STUDI DI MILANO, Milan (IT); POLITECNICO DI MILANO, Milan (IT)

(72) Inventors: Francesca Esposito, Rome (IT); John Robert Brucato, Rome (IT); Fabio Cozzolino, Rome (IT); Giuseppe Mongelluzzo, Rome (IT); Ciprian Ionut Popa, Rome (IT); Teresa Fornaro, Rome (IT); Andrea Meneghin, Rome (IT); Daniele Paglialunga, Rome (IT); Giovanni Pareschi, Rome (IT); Giampiero De Cesare, Rome (IT); Domenico Caputo, Rome (IT); Augusto Nascetti, Rome (IT); Francesca Costantini, Rome (IT); Nicola Lovecchio, Rome (IT); Lorenzo Iannascoli, Rome (IT); Mara Mirasoli, Bologna (IT); Elisa Michelini, Bologna (IT); Massimo Guardigli, Bologna (IT); Mario Clerici, Milan (IT); Daria Trabattoni, Milan (IT); Mara Biasin, Milan (IT); Diego Scaccabarozzi, Milan (IT)

(73) Assignees: ISTITUTO NAZIONALE DI ASTROFISICA (IT); UNIVERSITA' DEGLI STUDI DI ROMA "LA SAPIENZA" (IT); ALMA MATER STUDIORUM—UNIVERSITA' DI BOLOGNA (IT); UNIVERSITA' DEGLI STUDI DI MILANO (IT); POLITECNICO DI MILANO (IT)

( * ) Notice: Subject to any disclaimer, the term of this patent is extended or adjusted under 35 U.S.C. 154(b) by 648 days.

(21) Appl. No.: 18/017,802

(22) PCT Filed: Jul. 29, 2021

(86) PCT No.: PCT/IB2021/056928
§ 371 (c)(1),
(2) Date: Jan. 24, 2023

(87) PCT Pub. No.: WO2022/024035
PCT Pub. Date: Feb. 3, 2022

(65) Prior Publication Data
US 2023/0279509 A1 Sep. 7, 2023

(30) Foreign Application Priority Data
Jul. 29, 2020 (IT) ........................ 102020000018409

(51) Int. Cl.
| | |
|---|---|
| *C12Q 1/68* | (2018.01) |
| *C12P 19/34* | (2006.01) |
| *C12Q 1/6806* | (2018.01) |
| *C12Q 1/70* | (2006.01) |
| *G01N 1/22* | (2006.01) |
| *G01N 1/24* | (2006.01) |

(52) U.S. Cl.
CPC ............. *C12Q 1/70* (2013.01); *C12Q 1/6806* (2013.01); *G01N 1/2273* (2013.01); *G01N 1/24* (2013.01)

(58) Field of Classification Search
CPC ........................................................ C12Q 1/70
See application file for complete search history.

(56) References Cited

U.S. PATENT DOCUMENTS

| | | | |
|---|---|---|---|
| 2010/0230610 A1* | 9/2010 | Van Der Zaag ... | G01N 21/6454 250/200 |
| 2012/0174650 A1 | 7/2012 | Ariessohn et al. | |
| 2016/0258029 A1* | 9/2016 | Otsu ..................... | C12Q 1/689 |
| 2018/0164283 A1 | 6/2018 | Godula-Jopek et al. | |
| 2019/0212233 A1* | 7/2019 | Jovanovich ............. | C12N 1/06 |
| 2021/0299209 A1* | 9/2021 | Goren .................... | A61P 31/16 |

FOREIGN PATENT DOCUMENTS

| | | |
|---|---|---|
| WO | 2011003941 A1 | 1/2011 |
| WO | 2018210127 A1 | 11/2018 |
| WO | 2018210128 A1 | 11/2018 |

OTHER PUBLICATIONS

Po Ying Chia et al., "Detection of air and surface contamination by SARS-CoV-2 in hospital rooms of infected patients", Nature Communications, vol. 11, No. 1, May 29, 2020 (May 29, 2020), XP055737313.

* cited by examiner

*Primary Examiner* — Kenneth R Horlick
(74) *Attorney, Agent, or Firm* — The Belles Group, P.C.

(57) ABSTRACT

An apparatus for sampling and detecting a pathogen in air comprising a first air sampling module, a second module for the isolation of viral RNA and a third module for amplification and detection of the viral RNA; thanks to the integration between the modules the apparatus is compact and portable and can be used for in situ sampling of air in closed environments such as ambulances or hospital rooms, air in the external environment and air exhaled by patients.

19 Claims, 4 Drawing Sheets

APPARATUS AND METHOD FOR SAMPLING AND DETECTING A PATHOGEN IN AIR

CROSS-REFERENCE TO RELATED APPLICATIONS

This patent application is a U.S. national stage application under 35 U.S.C. § 371 of PCT application no. PCT/IB2021/056928, filed on Jul. 29, 2021, which claims priority from Italian Patent application Ser. No. 10/202,0000018409 filed on Jul. 29, 2020. The entire disclosure of the aforementioned priority applications are incorporated herein by reference in their entireties.

TECHNICAL FIELD

The present invention concerns an apparatus and a method for sampling and detecting pathogens in air. The invention is preferably applied in air sampling, mainly in closed environments such as A&E waiting rooms, hospital rooms, supermarkets, offices, lifts, undergrounds, etc. and in aerosol emissions produced directly by the respiratory tracts of a patient and in breathing and ventilation apparatus, for detecting pathogens in the air sampled. More specifically, the apparatus of the present invention allows the detection of viruses suspended in the air sampled by said apparatus, including the SARS-CoV-2 virus, which will be referred to below without loss of generality.

STATE OF THE PRIOR ART

In the current public health emergency caused by the global and uncontrolled spread of the SARS-CoV-2 virus, stringent control and prevention measures have to be introduced in order to limit the probability of contracting the disease.

Among these measures, accurate and timely methods for sampling and detecting the SARS-CoV-2 virus in the air are desirable. The fundamentally important role of detection of the SARS-CoV-2 virus in the air sampled, as a method that can effectively help to curb the spread of the pandemic, has been shown by various scientific studies that highlight the possible survival of the SARS-CoV-2 virus in the air for several hours and over long distances.

Following said scientific evidence, the World Health Organization recommends maintaining a distance between individuals of approximately 1 metre in order to limit the spread of SARS-CoV-2 virus infections. As reported in a recent study (L. Bourouiba, "Turbulent Gas Clouds and Respiratory Pathogen Emissions", JAMA Insight, 2020), these recommendations are the result of an estimate of the distances based on models, developed in the first half of the 1900s, according to which infection can occur via expiratory droplets having dimensions large enough to be deposited in the immediate vicinity of the infected individuals before evaporating, whereas the smaller expiratory droplets evaporate before they are deposited. However, the report shows that, following exhalation, sneezing and coughing, in addition to the droplets that follow semi-ballistic trajectories, a turbulent gas cloud is generated that transports within it a cluster of droplets in a wide range of dimensions. The damp and warm environment of the cloud, as opposed to the droplets being in isolation, contributes to prolonging the evaporation times of the droplets, extending their life time up to a factor of 1000 and increasing the distances travelled to approximately 7-8 m. The droplets that are deposited along the trajectory can contaminate surfaces, the others remain trapped in the cloud until it loses momentum and allows evaporation. Droplet residues or nuclei are therefore left and can remain in suspension for hours in the air. The length of time the droplets remain in the air is regulated by the ambient conditions and by any ventilation and conditioning systems operating.

This scientific evidence is supported by other studies such as, for example, the one carried out by N. van Doremalen et al., "Aerosol and Surface Stability of SARS-CoV-2 as compared with SARS-CoV-1", The New England Journal of Medicine, 2020, which reports the persistence of the SARS-CoV-2 virus in the aerosol for at least 3 hours.

In addition to the expiratory droplets, SARS-CoV-2 enters the air also simply by breathing, as shown by an American study that detected the SARS-CoV-2 virus in air samples collected at a distance of over 1.8 metres between two patients, or in operating theatres during operations on infected patients.

At the same time, the virus can survive for several hours in ventilation equipment and aeration systems. There is also evidence of the presence of the virus on various surfaces, from the floors to the walls of hospital rooms. From these surfaces, the virus could be re-circulated in the air, for example by walking on contaminated floors.

In addition to the droplets exhaled and the breath of infected persons, a further potential carrier for transmission of the virus is atmospheric particulate. Several studies show the possible link between pollution caused by atmospheric particulate and the spread of the SARS-CoV-2 epidemic, while in another study the virus was found on the particulate.

Hence the need to sample and analyse both the atmospheric particulate and the aerosol, including the aerosol emitted directly by persons potentially infected by SARS-CoV-2.

Following identification of the virus, targeted timely actions can be implemented aimed, for example, at sanitisation of the environment in which the air sampling was carried out and also of the neighbouring areas, identification of the persons who regularly visit said environment, carrying out diagnostic tests on them and directly diagnosing the virus infection if the air collected comes directly from the breath of a patient or asymptomatic persons, giving the apparatus of the present invention a diagnostic function not only of ambient type but also for medical use, alongside the commonly used nasopharyngeal swabs.

In the patent and non-patent literature, devices are known that separately perform sampling of the air with capture of the airborne pathogens and the detection of said pathogens based on chemical or biomolecular analyses or analysis of chemical-physical properties.

The devices belonging to the first category and therefore most commonly used for sampling the air and capturing the virus include solid impactors (for example Andersen or slit impactors) or liquid impactors (All-glass impingers—AGIs and similar), cyclonic samplers and filters.

As regards the methods for detecting pathogens, including viruses, alongside the traditional spectroscopic and microbiological techniques, there are the most recent devices that use lab-on-chip technology. In this regard, the patent WO2008/090578 describes an integrated system for chemical and/or biomolecular analysis that uses the lab-on-chip technology to perform, automatically and rapidly, complex analyses on small quantities of DNA. The DNA sample amplified by the polymerase chain reaction (PCR) is analysed by means of spectroscopic techniques in emission or absorption, and the response is translated into an electric pulse thanks to the optoelectronic sensors integrated in the chip.

However, the known devices cited above, like other similar ones, have some limitations. Firstly, the sampling and detection of pathogens are carried out in separate stages and with independent devices. This requires the intervention of an operator who can withdraw the sample collected in a first device and, subsequently, prepare the sample for analysis by means of a second device. Usually, the sample collected must be treated before being analysed. For example, from the air sample collected the biological material is isolated, from which the nucleic acids (RNA and DNA) are extracted, such as macromolecules which will undergo molecular testing in order to identify infectious agents. Also to implement said processing phases of the sample collected, specific devices are used. Therefore, the intervention of an operator and likewise the use of multiple specific devices which are often not compatible entails logistical problems, in the transfer of samples from the sampling device to the analysis device after the processing phase, criticalities connected with the reliability, quality and repeatability of the results with related expenditure of time and money. Secondly, the detection devices, like those used in the sample processing phase, are usually characterised by sophisticated and often bulky instrumental apparatus installed in specialist laboratories.

Consequently, analysis of the air sampled does not take place on site but in different places and at different times from the sampling, introducing complex and delicate mechanisms for storage and conservation of the sample and prolonging the timescales for ascertaining the presence of any pathogens contained in the air sampled.

WO 2018/210128 A1 describes an integrated device for sampling and detecting airborne pathogens.

The device comprises a sampling container where lysis of the pathogen and extraction of its nucleic acid take place, a device for amplifying the nucleic acid by Polymerase Chain Reaction (PCR), a device for detecting the pathogen and an automatic control system.

OBJECT OF THE INVENTION

One object of the present invention is to provide an integrated easily transportable apparatus able to carry out sampling of the air, processing of the sample collected and detection of pathogens contained in the sampled air, and which optimises the transport efficiency of the pathogen from collection to detection thereof.

In accordance with said object, the present invention concerns an apparatus according to claim 1.

The present invention also concerns a method according to claim 17.

Said invention therefore allows sampling and analysis of the air containing aerosol and/or atmospheric particulate, using one single compact, portable and semi-automatic apparatus which combines the functions of three modules. Therefore, said apparatus allows sampling and analysis of the air directly on-site, reducing times and costs connected with transport of the sample from the place of collection to the specialist analysis laboratories. More precisely, said apparatus allows the detection of pathogens contained in the sampled air, and preferably allows detection of the SARS-CoV-2 virus. Therefore, detection of the virus is timely and simplified, and the apparatus can be used also by unskilled operators, maintaining a high level of accuracy in terms of the results obtained.

BRIEF DESCRIPTION OF THE DRAWINGS

For a better understanding of the present invention some preferred embodiments are described below with reference to the attached drawings, in which.

PREFERRED EMBODIMENT OF THE INVENTION

Figures 1, 2:
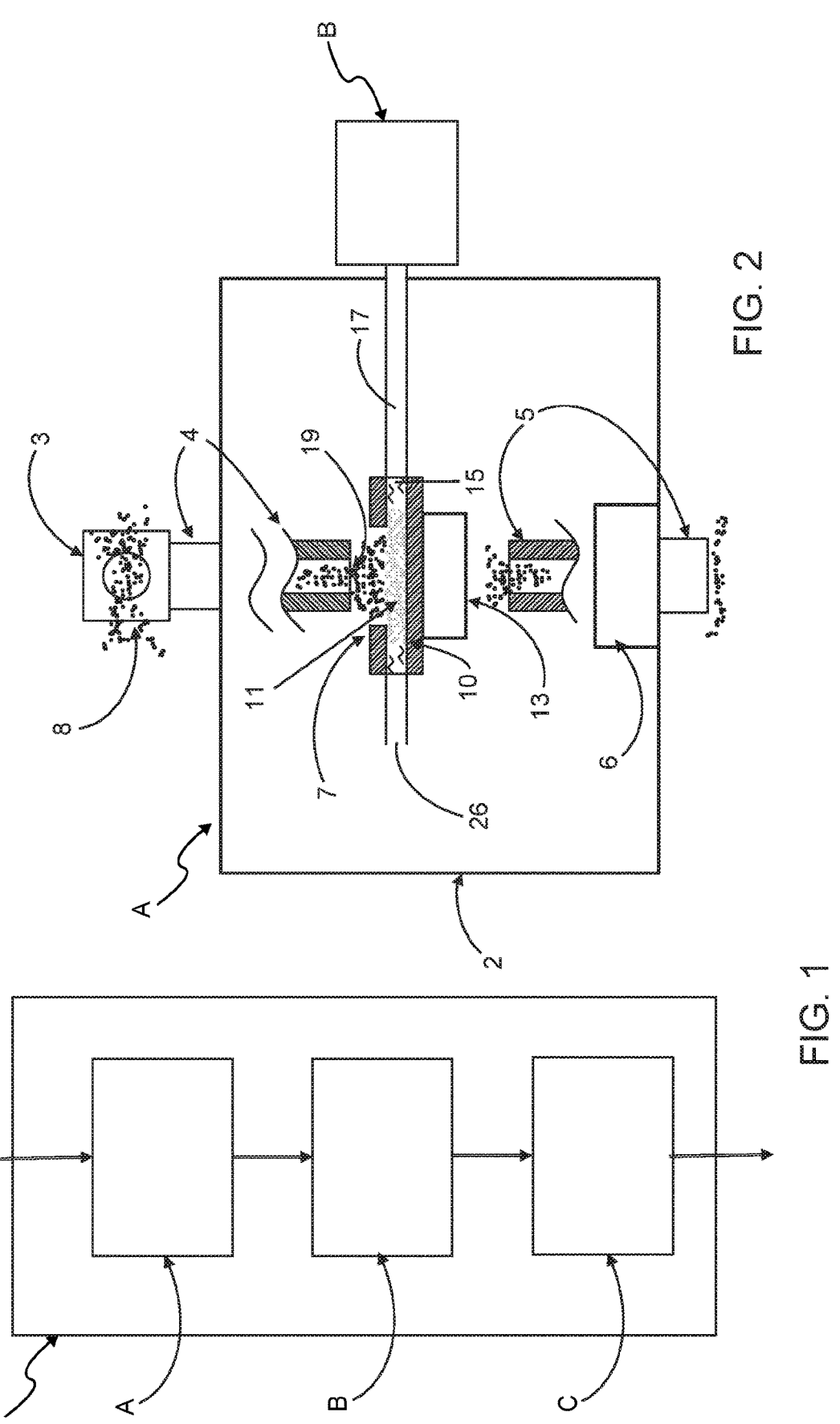
FIG. 1 is a block diagram of the apparatus according to the present invention.
FIG. 2 is a diagram of a first module of the apparatus of FIG. 1.

With reference to FIG. 1, the number 1 indicates overall an apparatus for sampling and detecting pathogens in air according to the present invention.

The apparatus 1 comprises in cascade a first module A for sampling the air, a second module B for the isolation and processing of biological material contained in the sampled air and a third module C for the analysis of said material.

FIG. 2 schematically illustrates an implementation example of the first module A forming part of the apparatus 1.

The first module A is able to sample particles and/or droplets the dimensions of which are between 100 nm and 40 μm. Said dimensional range includes both the atmospheric particulate with diameters smaller than 10 μm (PM10 and PM2.5), and the droplets contained in the aerosol emitted during respiration or via coughing and sneezing, with variable dimensions between less than 1 μm and approximately 16 μm.

The first module A comprises a casing 2 provided with an inlet opening 3, an inlet duct 4 communicating with the opening 3, an outlet duct 5 and a pump 6 arranged along the outlet duct 5 for determining an airflow through the inlet duct 4. Inside the casing 2 and in a position facing the inlet duct 4 a collector 7 is arranged designed to intercept the particles 8 entrained by the airflow sucked in.

The collector 7 can assume different embodiments according to the nature of the particles to be sampled. For example, if the main focus is the analysis of the droplets of an aerosol, as in the case of the analysis of the air exhaled by a patient or circulating in a ventilation system, the collector 7 comprises a support frame 10 and a membrane 11 made of humidified cellulose, for example compressed cotton wadding impregnated with a quantity of water between 2 ml and 4 ml, which occupies a central portion of the frame 10.

The membrane 11 of the collector 7 can be composed of other materials other than the cellulose, provided that the aerosol adsorbed is maintained in an aqueous solution.

The frame 10 is expediently metallic and is thermally regulated by a Peltier cell 13 so as to allow condensation of the aerosol on the membrane 11 and avoid re-evaporation of the aerosol droplets 8.

The mixture of aerosol droplets 8 intercepted by the membrane 11 and water present in said membrane 11 represents a biological solution 15 which then undergoes molecular testing.

The droplets 8 and any other substances not trapped in the collector 7 reach the outlet duct 5 and return to the external environment.

The ratio between the dimension of an outlet hole 19 of the inlet duct 4 and the dimension of the collector 7 must be calibrated so as to ensure the impact of the droplets 8 on the collector 7. Furthermore, the geometries in terms of length and diameter of the inlet duct 4 and outlet duct 5 respectively affect the sampling efficiency and the flow rate (volume sucked in per unit of time) of the first module A.

An implementation of the first module A illustrated in FIG. 2 by way of example comprises:

- an inlet duct 4 initially cylindrical with an internal diameter of 4 mm and then conical with an internal diameter of the outlet hole 19 of 1 mm;
- a collector 7 having cylindrical shape and diameter of 16 mm overall, with the cellulose membrane 11 having 10 mm diameter in the centre;
- a short distance of 4 mm between the outlet hole 19 of the inlet duct 4 and the collector 7;
- an outlet duct 5 having cylindrical shape, with internal diameter of 4 mm;
- a suction pump 6 able to generate a flow rate of 2 l/m.

The above-mentioned values can be modified by fluid-dynamic simulations provided that the dimensional sampling range of the droplets 8 remains unchanged and between 100 nm and 40 μm.

The biological solution 15, with volume in the range between 50 μl and 1000 μl, is sucked and transferred towards the second module B.

For this purpose, the module B, described in detail below, comprises at the inlet an interconnection chamber 18 connected to the membrane 11 by means of an interconnection system comprising one or more microtubes 17; in FIGS. 2 and 3 only one microtube 17 is illustrated for the sake of graphic simplicity.

The microtube 17 comprises one end connected to the inside of the collector 7, directly or via a needle inserted in the membrane 11, and an opposite end connected to the interconnection chamber 18 in the second module B.

Figure 3:
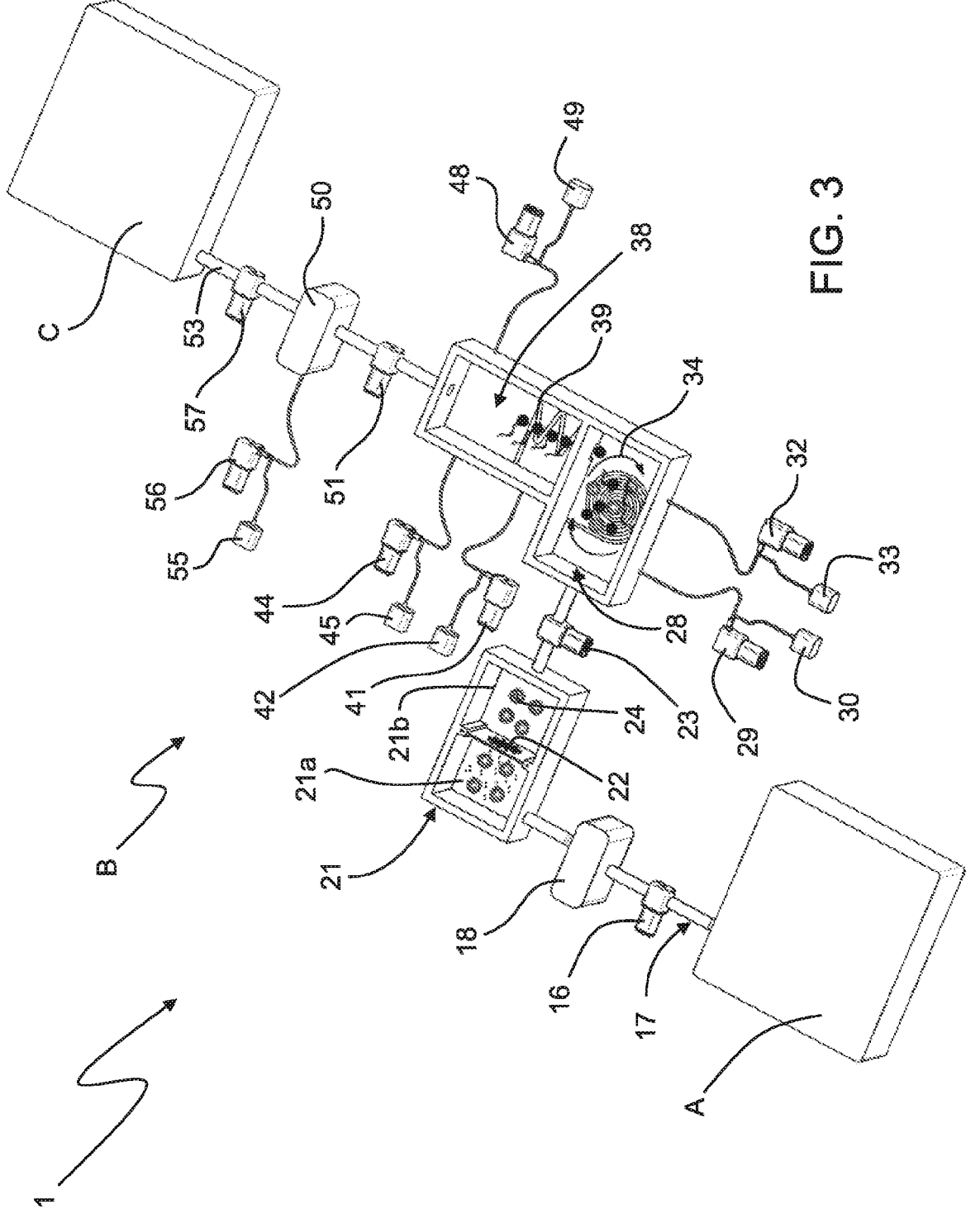
FIG. 3 is a schematic perspective view of the apparatus according to the present invention, with a perspective, schematic and exploded view of the components of a second module of the apparatus.

The interconnection system comprises a miniaturized peristaltic pump 16 which allows suction of the biological solution 15 from the membrane 11 in the first module A to the interconnection chamber 18 in the second module B (FIG. 3).

According to an embodiment variation of the invention, the collector 7 can be connected to a humidification system, if the aqueous component already present in the membrane 11 is not quantitatively sufficient, for example if the sampling protocol involves a relatively long sampling phase, during which the membrane 11 could dry out.

The humidification system can comprise, for example, a tank containing a distilled water reserve and a peristaltic pump (not shown in FIG. 2) connected to the collector 7 by means of a microtube 26.

According to another preferred embodiment of the invention, the first module A is configured for sampling atmospheric particulate. Said configuration entails replacement of the membrane 11 of the collector 7, used to trap the aerosol droplets 8, with a tray protected by a filter sized so as to retain the particles with dimensions larger than those of interest. The tray is connected to a humidification system as described above.

Therefore, the particulate that passes through the filter is collected by the water contained in the tray, from which it can be drawn by means of a microtube provided with needle if necessary as previously described.

Analogously to collection of the aerosol droplets 8, a biological solution, obtained by mixing the particulate trapped in the tray with the aqueous solution, is sucked into the second module B thanks to the interconnection system described above.

FIG. 3 illustrates overall the second module B, which comprises a series of miniaturized chambers in which specific phases of the isolation and processing of the biological material starting from the biological solution 15 are carried out, in particular the steps for:

- filtering the biological solution 15 coming from the first module A;
- isolating and concentrating the viral RNA by means of lysis reagents and magnetic beads;
- extracting the viral RNA in a small volume (5-50 μl) of eluant solution which is sent to the third module C.

In particular the second module B comprises a filtration chamber 21 split into a sub-chamber 21a connected to the interconnection chamber 18 and a sub-chamber 21b separated from the sub-chamber 21a by a transverse wall comprising a filter 22 configured to retain particles having dimensions greater than or equal to 0.5 μm.

The second module B furthermore comprises a reaction chamber 28 in which isolation of the virus dispersed in the filtered solution 24 follows a process of release of the viral RNA.

The biological solution 15 is sucked from the interconnection chamber 18 to the reaction chamber 28 by a peristaltic pump 23 located downstream of the sub-chamber 21b. Therefore, the sub-chamber 21b represents the centre for the collection of a filtered biological solution 24.

The solid particles retained by the filter 22 can be removed by means of a suction system not illustrated.

The reaction chamber 28 is selectively connected to a tank 30 containing lysis and binding reagents by means of a pump 29, and to a tank 33 containing magnetic beads suspended in water by means of a pump 32. The above-mentioned reagents and the bead suspension, in addition to other substances described below, are available in kit under the trade name Dynabeads® SILANE Viral NA produced by ThermoFisher.

A magnetic stirring device 34 is arranged in the reaction chamber 28, said device being designed to generate, when excited, an oscillating magnetic field having the purpose of stirring the reaction mixture contained in the reaction chamber 28.

The second module B comprises an RNA extraction chamber 38 connected to the reaction chamber 28 and housing a coil 39 (or permanent magnets) configured to define a magnetic extraction path for transport of the beads to which the viral RNA is bound. A tank 42 containing a buffer washing solution and a tank 45 containing an elution reagent are selectively connected to the extraction chamber 38 by means of respective pumps 41, 44 (said products form part of the kit mentioned above). A further pump 48 is designed to remove the supernatant and buffer washing solution from the extraction chamber 38 and convey them towards a discharge tank 49.

The second module B comprises an interconnection chamber 50 designed to receive an RNA solution from the extraction chamber 38 by means of a pump 51, and reagents for use in the subsequent module C, as will be better described below.

7

Figure 4:
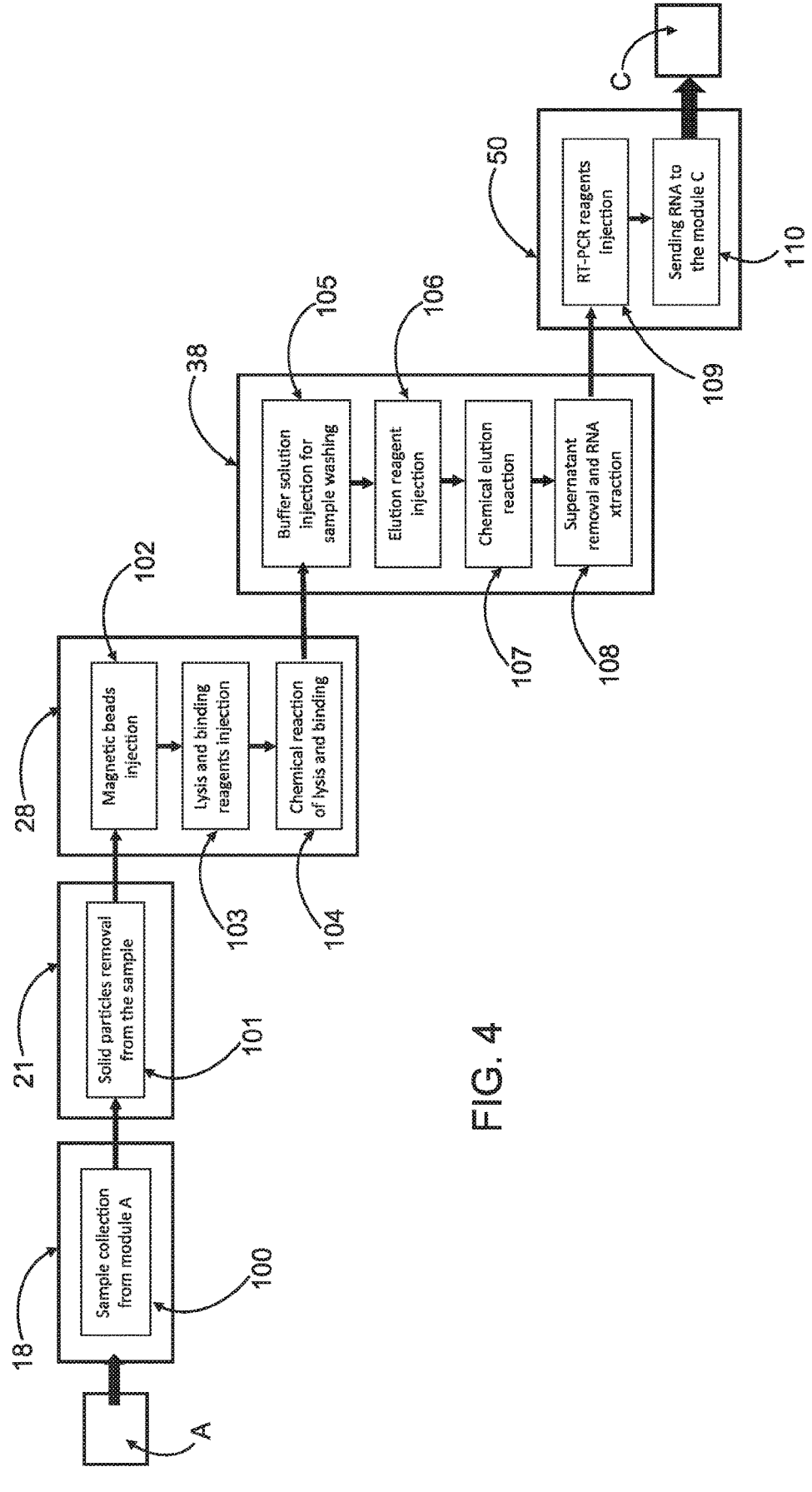
FIG. 4 is a flow diagram illustrating the various sample processing phases that take place in the second module.

The operation of the second module B, already partly evident from the above, is described below with reference to FIG. 4, which illustrates the various phases with reference to the chambers of the second module B in which they occur.

The biological solution 15, coming out of the first module A, is sucked by the pump 16 and collected in the interconnection chamber 18 (block 100). The sample is then conveyed into the filtration chamber 21 where a filtering step takes place (block 101) in which the solid particles present in the air and collected by the first module A are removed. The filtered solution 24 is then sent to the reaction chamber 28 where the following phases occur in sequence: input of the magnetic beads (block 102), input of the reagents for the lysis and the binding (block 103), and lysis reaction of the viral capsid and binding of the beads with the viral RNA released (block 104).

At the end of the reactions, the sample is sent through the magnetic path 39 into the RNA extraction chamber 38 where it is washed by the buffer solution (block 105) pumped in by the pump 41. Subsequently the elution reagent is introduced into the RNA extraction chamber 38 (block 106) by means of the pump 44, thus starting the elution phase (block 107). Once the elution phase has been completed, requiring a few minutes, the supernatant is eliminated (block 108) by means of the pump 48 while the RNA sample extracted 52 is sent towards the interconnection chamber 50 by means of a pump 51.

Expediently, the interconnection chamber 50 is connected to a tank 55 containing a mixture of reagents for amplifying the RNA as described below by means of a pump 56 (block 109). A reactive mixture, as a product of the interaction between the RNA solution 52 and the amplification reagents, is sent to the module C (block 110).

The chambers where the various phases take place can be appropriately temperature-controlled.

The interconnection chamber 50 is connected to the third module C by means of an interconnection system comprising a pump 57 and a microtube 53 (FIG. 3).

Figure 5:
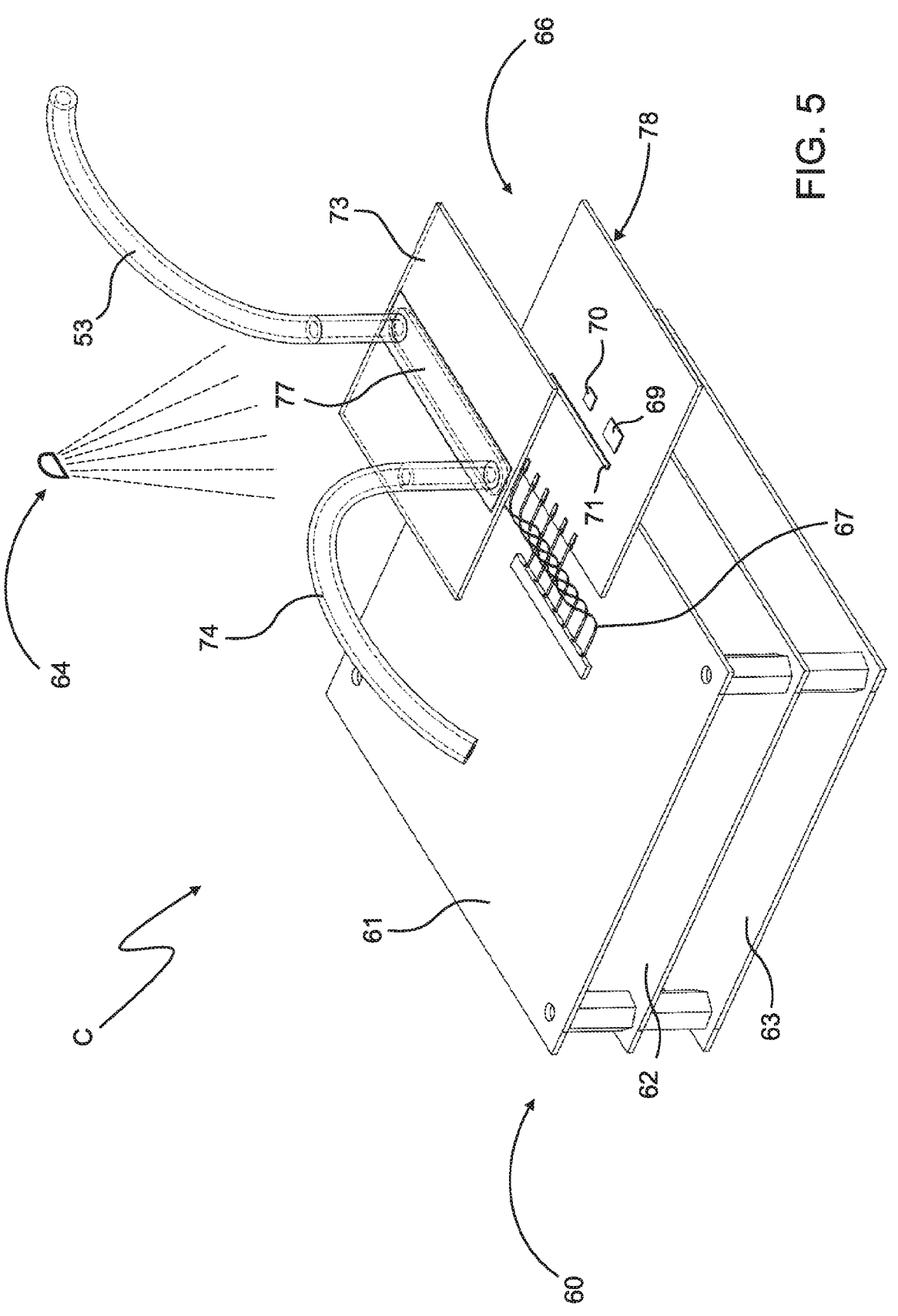
FIG. 5 is a schematic perspective view of a third module of the apparatus.

The third module C is schematically illustrated in FIG. 5 and comprises a lab-on-chip device 66 for amplifying and detecting the viral RNA in real time and a reading, control and interface electronic unit 60 for acquiring and processing signals from the lab-on-chip device 66.

The lab-on-chip device 66 comprises one single monolithic substrate or several substrates coupled permanently or temporarily, inside which the following are integrated:

one or more thin-film optical sensors 69 (photodiodes or phototransistors or multi-junction devices) made of hydrogenated amorphous silicon (a-Si:H);

one or more thin-film temperature sensors 70 (single layers of intrinsic or doped material or diodes or multi-junction devices) made of a-Si:H;

one or more resistive heaters 71 made of metal films or transparent conductive oxides (for example indium and tin oxide) or a combination of the two;

a microfluidic unit 73 for containing and treating the samples during the analytical phase; and one or more access points to the microfluidic network 73 for introducing samples and reagents and if necessary for the removal thereof.

In particular, the microfluidic unit 73 can be composed of a network of low-cost disposable microtubes or permanent microtubes that can be reused after the implementation of appropriate cleaning and/or sterilization procedures.

In the example illustrated, the microfluidic unit 73 comprises a microfluidic network 77 composed of a simple microfluidic channel connected at the inlet to the microtube 53, from which it receives the sample to be treated together with the additional reagents, and at the outlet to a microtube 74 that can be connected to a waste tank not illustrated.

Alternatively, the microfluidic network 77 can be more complex and comprise various microchannels and microtanks, for example formed of wells of appropriate volume.

Detection of the amplification of the viral RNA can be carried out in fluorescence or in chemiluminescence or in bioluminescence. In the example illustrated the detection is carried out in fluorescence, and the third module (C) also comprises an excitation radiation source 64.

The materials used for the lab-on-chip device 66 comprise, and are not limited to, one or more of the following materials: glass, polymer resins, polydimethylsiloxane (PDMS), cyclic olefin copolymers (COC), pressure-sensitive adhesives (PSA), silicon.

In the example illustrated, the microfluidic unit 73 is made of COC with micromilling sealed by pressure-sensitive adhesive tape.

Once the RNA solution 52 and the reagents have been loaded in the microfluidic channel 77, the analytical phase of amplification of the viral RNA can be initiated via the implementation of known techniques such as PCR, LAMP, LAMP-BART, RT-PCR, RT-LAMP and others.

In the example illustrated, the on-chip sensors 69, 70 and the on-chip heater 71 are expediently obtained on opposite faces of a sheet of glass 75 to form a System on Glass (SoG) coupled with the microfluidic unit 73, for example as described in the scientific article B. B. Bruijns et al., "On-chip real-time monitoring of multiple displacement amplification of DNA", Sensors and Actuators B: Chemical, Elsevier B. V., 2019.

The electronic unit 60 is structured on several levels. A first level is represented by an input/output board 61, below which a control board 62 is located. The last level consists of an interface board 63 which establishes connection between the lab-on-chip device 66 and the user interface systems (light indicators, display, computer interface). The lab-on-chip device 66 is connected to the input/output board 61 of the electronic unit 60 via a series of electrical contacts 67 which emerge from the input/output board 61.

The electrical contacts 67 conduct the following signals or voltages:

bias voltage of the optical sensors 69 generated by the input/output board 61;

current generated by the optical sensors 69 which is measured by the input/output board 61;

bias current of the temperature sensors 70 generated by the input/output board 61;

voltage drop on the temperature sensors 70 which is measured by the input/output board 61;

current for actuating the heater 71 provided by the input/output board 61 based on a control algorithm according to the temperature measured.

The input/output board 61 also contains low-noise transimpedance amplifiers, low-noise analog-digital converters, low-noise bias voltage generators between 0 and 5 V, low-noise bias current generators between 1 nA and 0.1 mA, high-efficiency current generators between 10 mA and 1 A.

The control board 62 contains a microcontroller or DSP or microprocessor with external interface circuitry for management of the protocol to be implemented on the lab-on-chip device 66 via the input/output board 61, and management of the ancillary systems present in the apparatus 1, for example the microfluidic pumps of the second module B.

The interface board 63 contains the electronics for management of the user interface (display, optical or acoustic indicator systems, data interface towards an external computer, etc.).

The boards 61, 62 and 63 or a sub-assembly thereof can be implemented on one single board, or the single boards can be created by combining several modules.

The excitation radiation source 64, comprised in the third module C, illuminates the lab-on-chip device 66 containing the sample in the microfluidic channel 77 and the optical sensors 69. In particular, the sample to be detected comprises fluorescent substances (for example fluorophores) which emit light in fluorescence following excitation by absorption of radiations having specific wavelengths coming from the radiation source 64. Preferably, the radiation source 64 emits UV radiations in resonance with the fluorescent substances comprised in the sample. The radiation source 64 can consist of LEDs.

Expediently, the optical sensors 69 are provided with interferential filters which absorb the radiations coming from the radiation source 64 and transmit the radiation emitted in fluorescence by the sample.

Further technical details can be found in the article cited and in the relative Supplementary Material.

The analysis method implemented in the third module C, in which the viral RNA is amplified by Reverse Transcriptase Polymerase Chain Reaction (RT-PCR), by way of example entails the following steps:

preparation of the following reactive mixture (in the interconnection chamber 50):

0.5 μl of Primer mix 0.2 μl of Reverse transcriptase enzyme,

5 μl of Master mix (contains DNA-polymerase oligonucleotides and MgCl2), 1.33 μL of fluorophore (Sybr Green/$[Ru(phen)_2(dppz)]^{2+}$ with concentration $10^{-5}$ M), 3 μL of solution of SARS-COV-2 virus RNA, (the reagents listed above are commercially available and can be purchased, for example, from Promeda Corporation);

loading of the reactive mixture in the microfluidic channel 77;

initiation of the analytical procedure implemented via the lab-on-chip device 66 and the electronic unit 60 connected to the lab-on-chip device 66 by means of the electrical contacts 67. In the specific example with the reagents indicated the procedure entails:

one step at 45° C. for 45 minutes;

one step at 95° C. for 2 minutes;

40 thermal cycles:

95° C. for 15 seconds;

60° C. for 60 seconds.

the thermal control is carried out via use of the temperature sensors 70 and the heater 71 and if necessary an external cooling system (for example a fan not shown in FIG. 5).

the constant or intermittent ignition of the radiation source 64, throughout the process, and the signal re-emitted by the fluorophore is constantly monitored by the optical sensors 69.

determination of the presence and if necessary quantification of the viral RNA in the sample is carried out by detecting the variation in the photocurrent generated by the optical sensors 69.

Basically, a sample consisting of a small volume of purified viral RNA enters the microfluidic unit 73 by means of the inlet microtube 53, together with the relative reagents.

Drawing of the sample from the interconnection chamber 50 to the third module C is controlled by the electronic system which drives the active components of the lab-on-chip device 66 and of the off-chip ancillary systems present in the apparatus 1, and in particular in the second module B (microfluidic pumps, fans, etc.). The viral RNA, deposited on the lab-on-chip device 66, is amplified by means of Reverse Transcriptase Polymerase Chain Reaction (RT-PCR) or by means of Reverse Transcription Loop-mediated isothermal amplification (RT-LAMP, RT-LAMP-BART).

Once an amplification of viral RNA has been obtained sufficient for the molecular testing, the detection phase can be initiated. In the example illustrated, the SARS-COV-2 virus RNA is detected in fluorescence. In fact, a fluorophore is added to the multiplied viral RNA, said fluorophore manifesting an intense photoluminescence only when it binds to the SARS-COV-2 virus RNA. Alternatively, the detection can be carried out in chemiluminescence or bioluminescence.

Since the detection is based on emission spectroscopy techniques, to increase the sensitivity it is necessary to reduce the interfering radiations coming from sources external to the lab-on-chip device 66. Therefore, the third module C is preferably protected by a sealed opaque casing which blocks the interfering radiations.

From an examination of the characteristics of the present invention, the advantages it offers are evident.

In particular, the apparatus of the invention carries out in an integrated manner each phase of the process of sampling, processing and detection of the pathogen, allowing all the above-mentioned phases to be performed in situ efficiently and rapidly. In particular, the transport efficiency of the pathogen from collection to detection is optimised via the combined use of an improved collector and magnetic beads for transport of the nucleic acid after the lysis and towards the amplification system by means of PCR.

The invention claimed is:

1. An apparatus for sampling and detecting a pathogen in air comprising:

a first air sampling module configured to collect a sample of airborne particles and comprising an inlet duct for sucking an airflow from an external environment and a collector comprising a humidified membrane to intercept the airflow and retain said particles;

a second sample processing module comprising a reaction chamber, which is connected with a first tank containing at least one lysis and binding reagent by means of a first pump and is connected to a second tank containing magnetic beads by means of a second pump;

a third module comprising a lab-on-chip device and an electronic unit for the detection of pathogens;

a first fluidic interconnection configured to transfer the sample from the first module to the second module;

a second fluidic interconnection configured to transfer the nucleic acid of the sample from the second module to the third module; and at least an automatic control unit of said modules, the first fluidic interconnection, and the second fluidic interconnection.

2. The apparatus according to claim 1, wherein the humidified membrane is made of cellulose.

3. The apparatus according to claim 1, wherein the collector comprises a tray protected by a filter.

4. The apparatus according to claim 1, wherein the inlet duct is configured to convey particles having size between 100 nm and 40 μm towards the collector.

5. The apparatus according to claim 1, wherein the first fluidic interconnection comprises an interconnection chamber and a pump connected to the collector by at least one microtube to draw an aqueous solution containing said particles from the collector to the interconnection chamber.

6. The apparatus according to claim 1, wherein the second module includes a filtration chamber equipped with a filter configured to retain solid particles larger than the size of the pathogen.

7. The apparatus according to claim 1, wherein the reaction chamber is equipped with a stirring device; and wherein the second module comprises a nucleic acid extraction chamber defining a magnetic extraction path for the magnetic beads bound to the nucleic acid.

8. The apparatus according to claim 1, wherein the first fluidic interconnection and the second fluidic interconnection comprise respective tanks and related pumps for transferring a solution containing the sample from the first module to the second module and for transferring a solution containing at least the nucleic acid of the sample from the second module to the third module.

9. The apparatus according to claim 1, wherein the lab-on-chip device includes:

at least one thin-film optical sensor made of hydrogenated amorphous silicon (a-Si:H);

at least one thin-film temperature sensor of a-Si:H; and at least one resistive heater made of metal films, transparent conductive oxides or combinations thereof.

10. The apparatus according to claim 1, comprising a microfluidic unit coupled to the lab-on-chip device and connected to the second fluidic interconnection; and wherein the microfluidic unit comprises at least one seat for containing the nucleic acid of the sample and reagents for an amplification of the nucleic acid.

11. The apparatus according to claim 1, wherein the electronic unit comprises input/output means for connection with the lab-on-chip device, control means for controlling at least the lab-on-chip device and interface means for connection with at least one user interface device.

12. The apparatus according to claim 11, wherein the control means control at least one device of the second module.

13. The apparatus according to claim 1, wherein the third module includes an excitation radiation source for detecting an amplification in fluorescence.

14. A method for sampling and detecting a pathogen in air comprising the steps of:

air sampling for collecting a sample of airborne particles in a collector comprising a humidified membrane;

sample processing for extracting a nucleic acid from said sample by means of lysis and binding of the nucleic acid with magnetic beads; and nucleic acid analysis for the detection of pathogens;

said steps being carried out in sequence within an integrated automatically controlled apparatus as claimed in claim 1.

15. The method according to claim 14, further comprising sample filtering by means of a filter configured to retain solid particles larger than the size of the pathogen prior to the step of sample processing.

16. The method according to claim 14, wherein the nucleic acid analysis comprises operations of amplifying the nucleic acid of the sample by polymerase chain reaction (PCR) and detecting the pathogen whose nucleic acid is amplified by fluorescence or chemiluminescence or bioluminescence.

17. The method according to claim 16, wherein the operation of amplifying the nucleic acid of the sample is activated by the reaction between the nucleic acid of the sample and specific reagents for said nucleic acid.

18. The method according to claim 14, wherein the nucleic acid of the sample is RNA.

19. The method according to claim 17, wherein specific reagents amplify the RNA of SARS-CoV-2 virus by Reverse Transcriptase Polymerase Chain Reaction (RT-PCR).

* * * * *